US005705700A

United States Patent [19]

Darsow et al.

[11] Patent Number: 5,705,700
[45] Date of Patent: Jan. 6, 1998

[54] PROCESS FOR PREPARING A MIXTURE OF CYCLOHEXYLAMINE AND DICYCLOHEXYLAMINE

[75] Inventors: Gerhard Darsow, Krefeld; Gerd-Michael Petruck, Erkrath; Wilfried Niemeier, Krefeld, all of Germany

[73] Assignee: Bayer Aktiengesellschaft, Leverkusen, Germany

[21] Appl. No.: 755,512

[22] Filed: Nov. 22, 1996

[30] Foreign Application Priority Data

Dec. 8, 1995 [DE] Germany ............ 19 545 884.2

[51] Int. Cl.⁶ ............................................. C07C 209/72
[52] U.S. Cl. ............................................. 564/450
[58] Field of Search ............... 564/450, 451, 564/457, 461, 449

[56] References Cited

U.S. PATENT DOCUMENTS

| 3,636,108 | 1/1972 | Brake . |
| 4,057,513 | 11/1977 | Biedermann et al. . |
| 4,429,155 | 1/1984 | Göetz et al. . |
| 4,914,239 | 4/1990 | Kiyuma et al. . |
| 5,322,965 | 6/1994 | Immel et al. . |
| 5,371,294 | 12/1994 | Immel et al. ............ 564/450 |
| 5,386,060 | 1/1995 | Immel et al. . |
| 5,545,756 | 8/1996 | Vedage et al. ............ 564/450 |
| 5,599,997 | 2/1997 | Hearn et al. ............ 564/450 |

FOREIGN PATENT DOCUMENTS

| 0053818 | 6/1982 | European Pat. Off. . |
| 0501265 | 9/1992 | European Pat. Off. . |
| 0503347 | 9/1992 | European Pat. Off. . |
| 1530477 | 7/1968 | France . |
| 805518 | 5/1951 | Germany . |
| 1106319 | 1/1958 | Germany . |
| 1106319 | 5/1961 | Germany . |
| 318068 | 4/1965 | Japan . |
| 04018935 | 1/1992 | Japan . |
| 969542 | 9/1964 | United Kingdom . |

*Primary Examiner*—Brian M. Burn
*Attorney, Agent, or Firm*—Sprung Kramer Schaefer & Briscoe

[57] ABSTRACT

To prepare a mixture of cyclohexylamine and dicyclohexylamine by catalytic hydrogenation of aniline at elevated temperature and elevated $H_2$ pressure, the catalyst system used comprises two reduced, unsupported catalysts A and B which are prepared from pressed element (hydr)oxide powders. Catalyst A comprises one or more of Fe, Co, Ni, also Mn, Cu and one or more of Ca, Sr, Ba. Catalyst B comprises one or more of Fe, Co, Ni, also Mn, Si and Mg.

18 Claims, No Drawings

PROCESS FOR PREPARING A MIXTURE OF CYCLOHEXYLAMINE AND DICYCLOHEXYLAMINE

BACKGROUND OF THE INVENTION

1. Field of the Invention

The invention relates to a process for preparing a mixture of unsubstituted or substituted cyclohexylamine and unsubstituted or substituted dicyclohexylamine in variable amounts by catalytic liquid-phase hydrogenation of unsubstituted or substituted aniline with hydrogen at elevated temperature using a system of two reduced, unsupported pressed oxidic fixed-bed catalysts. Unsubstituted or substituted cyclohexylamines and dicyclohexylamines are used for preparing aging inhibitors for rubbers and plastics, as corrosion inhibitors in aqueous solution, and also as precursors for textile auxiliaries and crop protection agents.

2. Description of the Related Art

It is known that cyclohexylamine can be prepared by pressure hydrogenation of aniline. This hydrogenation is mainly carried out using expensive noble metal catalysts, for example as described in U.S. Pat. No. 3,636,108 an alkali-moderated Ru catalyst, with $NH_3$ and, if desired, a solvent being used in addition. A further process for the pressure hydrogenation of aniline to give cyclohexylamine is described in DE-B 1 106 319, where an Ru catalyst is likewise used. In this process, dicyclohexylamine also formed is added back to the starting material. However, because of the simultaneous formation of cyclohexane, the process achieves only a mode-rate yield. According to EP-B 53 818, supported Pd catalysts are more favorable than Ru catalysts; the catalysts described therein contain additives originating either from a group of basic compounds of the alkali metals, alkaline earth metals and rare earth metals or from a group which comprises the metals Fe, Ni, Co, Mn, Zn, Cd and Ag. These catalysts allow the reduction of substituted anilines to give the corresponding cyclohexylamines; however, the corresponding dicyclohexylamines are all missing. This applies likewise to Co catalysts containing a basic additive (GB 969 542) and to Raney Co (IP 68/03 180).

In the pressure hydrogenation processes described for aniline, the dicyclohexylamine is, if it is formed at all, formed only as a by-product in addition to the cyclohexylamine. To obtain dicyclohexylamine in larger amounts, it is prepared by a separate process. Thus, it can be obtained, for example, by pressure hydrogenation of diphenylamine using an $Ru/Al_2O_3$ catalyst (DE-B 1 106 319 above). Dicyclohexylamine is also formed in the reaction of cyclohexanone with cyclohexylamine in the presence of Pd on carbon under a hydrogen pressure of 4 bar (FR 1 530 477).

In a cumbersome process, dicyclohexylamine can be obtained from the hydrogenation product of aniline over an Ni catalyst by fractional condensation. From the remaining mixture, part of the ammonia also formed is removed and the remainder is returned to the reaction (DE-C 805 518).

A problem common to all these processes for the ring-hydrogenation of aromatic amines is the sometimes considerable formation of cyclohexane as by-product which cannot be reused. There was therefore still the desire to develop a new process which could also be used on an industrial scale and by means of which both cyclohexylamine and dicyclohexylamine could be prepared in a desired ratio, in which process the loss resulting from the undesired formation of cyclohexane is suppressed and, furthermore, the life of the catalyst used is improved.

EP-A 501 265 discloses a process for preparing unsubstituted or substituted cyclohexylamine and unsubstituted or substituted dicyclohexylamine by catalytic hydrogenation of unsubstituted or substituted aniline using a catalyst comprising Ru, Pd or a mixture of both metals applied to a support of niobic acid or tantalic acid or a mixture of both. EP-A 503 347 discloses a further process for preparing unsubstituted or substituted cyclohexylamine and unsubstituted or substituted dicyclohexylamine by hydrogenation of a correspondingly substituted aniline using a catalyst in which an α- or γ-$Al_2O_3$ as support is first treated with at least one compound of rare earth metals and with at least one compound of manganese and then with at least one Pd compound. The preparation of the catalysts in these processes of EP-A 501 265 and EP-A 503 347 is technically complicated and their use is expensive since the recovery of the noble metals from the complex mixtures of substances after the catalyst is exhausted creates considerable problems which were not recognized at the beginning. In addition, in this process the ratio of the cyclic amines which can be prepared is shifted too much in the direction of higher proportions of dicyclohexylamine. Finally, the life of the catalysts used in the last-named processes is too low at from 3000 to 4000 hours, so that the catalysts were not able to meet expectations.

It has now surprisingly been found that the abovementioned requirements can be met by the use of a system comprising two inexpensive oxidic fixed-bed catalysts which are free of inactive support material and can therefore be readily worked up and disposed of.

SUMMARY OF THE INVENTION

The invention accordingly provides a process for preparing a mixture of cyclohexylamine and dicyclohexylamine of the formulae

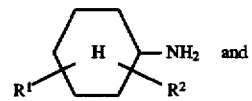 (I)

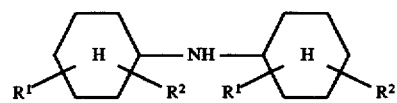 (II)

by catalytic hydrogenation of aniline of the formula

 (III)

where, in the formulae,
$R^1$ and $R^2$ are, independently of one another, hydrogen, $C_1$–$C_4$-alkyl or $C_1$–$C_4$-alkoxy,
at a reaction temperature of from 140° to 260° C. and an $H_2$ pressure of from 10 to 400 bar, wherein the catalyst system used comprises two reduced, unsupported catalysts A+B comprising pressed element (hydr)oxide powders in which the following element proportions are present:
for catalyst A:40–60% by weight of one or more of Fe, Co, Ni;
10–20% by weight of Mn; 0.05–1.5% by weight of Cu; and 0.2–5% by weight of one or more of Ca, Sr, Ba; and
for catalyst B:30–50% by weight of one or more of Fe, Co, Ni; 3–10% by weight of Mn; 5–15% by weight of Si; and 2–8% by weight of Mg;
where, in A and B, the remainder to 100% by weight is oxygen and the percentages are based on the total weight of the respective catalyst A or B.

DETAILED DESCRIPTION OF THE INVENTION

From the element group Fe, Co, Ni, preference is given to using Co or Ni or a Co/Ni mixture and particular preference is given to using Co.

From the group Ca, Sr, Ba, preference is given to using Sr or Ba or an Sr/Ba mixture and particular preference is given to using Ba.

To prepare the catalysts A and B, powders of oxides of the specified elements are used. The alkaline earth metals mentioned can also be used in the form of their hydroxides. Si can also be used as silica gel. In the case of the heavy metals, it is likewise possible to replace the oxide powders by hydroxide powders which are either used as such or are obtained individually or jointly as hydroxides after precipitation from aqueous solutions of metal salts in a known manner. Preferably, oxide powders of the specified elements are used. Such powders are mechanically mixed with one another in such amounts that they fulfil the weight ratios indicated above. The remainder to 100% by weight is always the proportion of oxygen, and all percentages by weight are based on the total weight of the oxidic, support-free compact. The mixture of the powders is then pressed on tabletting or pelletizing machines under high pressure, with it also being possible to use graphite, adhesives or both in amounts of 0.5–1% by weight, based on the total weight of the powders to be pressed, to improve the adhesion of the powder. Examples of shapes of such compacts are pellets, spheres or cylindrical granules having dimensions of 1–10 mm, preferably 3–7 mm. Tabletted bodies can additionally be provided with an axial hole to increase the external surface area. Viewed macroscopically, such pressed bodies have a smooth surface. The pressed bodies have a high compressive strength on the surface of the body. Thus, pellets or cylindrical granules have a compressive strength of 200–800N/cm$^2$, preferably 250–600N/cm$^2$, on the flat pressed surfaces, and pellets, spheres or cylindrical granules have a compressive strength on the curved pressed surfaces of 50–200N (measured as force), preferably 80–140N. The internal surface area of the pressed bodies used is 30–200 m$^2$/g, preferably 80–160 m$^2$/g. The compressive strength of the support-free shaped bodies can be determined in accordance with DIN 50 106. The determination of the internal surface area is carried out by the method of F. M. Nelson and F. T. Eggertsen, Analyt. Chem. 30 (1958), pp. 1387–1390 or by the method of S. L Gregg and K. S. W. Sing, Adsorption Surface Area and Porosity, Academic Press, London 1982, Chapters 2 and 6.

Using the catalysts described, the process of the invention gives a mixture of unsubstituted or substituted cyclohexylamine and unsubstituted or substituted dicyclohexylamine, with, surprisingly, the ratio of the two amines being able to be changed as a function of the hydrogenation temperature such that with rising temperature more unsubstituted or substituted dicyclohexylamine and less unsubstituted or substituted cyclohexylamine is formed and with falling temperature the reverse effect is achieved.

The temperature range for the process of the invention is 140°–260° C., preferably 160°–230° C. The process is carried out at an H$_2$ pressure of 10–400 bar, preferably 20–350 bar, particularly preferably 100–300 bar.

The process of the invention can be carried out, for example, batchwise in an autoclave or continuously in the downflow mode, but in any case in the liquid phase. For industrial purposes, the process is preferably carried out continuously, with the catalyst beds being fixed. The hydrogenation reactors for a continuous downflow-mode reaction can be individual high-pressure tubes of steel or a steel alloy which are completely or partially filled with the shaped bodies. In the case of relatively large tube cross-sections it can also be useful to use the support-free shaped bodies on trays such as wire baskets or similar internal fittings. Furthermore, it is also possible to use high-pressure tube bundles within a common jacket, with the individual tubes again being completely or partially filled with the shaped catalyst bodies.

The specified catalysts A and B can, in principle, i.e., used in the form of a mixture; this is also the only sensible form in the case of a batchwise autoclave procedure. The weight ratio can be adjusted from 0.5 A: 9.5 B to 9.5 A: 0.5 B. When carrying out the hydrogenation in a downflow mode, it has been found to be advantageous for the starting material to be hydrogenated first to pass through a bed of the catalyst A and then through a bed of the catalyst B. Here, A and B can be arranged in separately introduced layers in the same high-pressure tube or in two high-pressure tubes which are charged differently and are connected in series. In such an arrangement too, the specified weight ratio of A:B applies. However, in principle it is also possible in the downflow-mode process for the starting material to pass first through the catalyst B and only then through the catalyst A. Likewise, in the downflow-mode process it is also possible in principle to use a mixture of A and B.

The pressed, unsupported catalysts A and B are reduced by hydrogen and thus activated. This is in principle possible simultaneously with the hydrogenation of the starting material used, but here a longer running-in phase is required before the catalysts reach their full activity and thus the highest possible space-time yield is obtained. It is therefore advantageous to reduce the two catalysts A and B either separately or together before starting material is passed through. This activating reduction with hydrogen is carried out in a temperature range of 160°–240° C. and a pressure range of 10–400 bar. Here, the atmospheric oxygen initially present is first completely removed by means of an inert gas such as nitrogen, argon, methane or ethane before a proportion of 10–15% by volume of hydrogen is added to the inert gas. Owing to its ready availability, nitrogen is the preferred inert gas. The proportion of inert gas is then continually decreased over a set period of time, for example 24 hours, and the inert gas is finally completely removed so that activation and reduction is carried out using pure hydrogen. The reduction is complete when the catalyst no longer consumes hydrogen and as a result water of reaction is no longer formed.

In the downflow-mode procedure, the weight hourly space velocity is 0.1–3 kg, preferably 0.15–1.5 kg, of unsubstituted or substituted aniline per liter of catalyst and hour. The unsubstituted or substituted aniline used can be diluted with a suitable reaction-inert solvent, for example with cyclohexane or cyclohexanol, in an amount of 10–100% by weight, preferably 10–40% by weight, based on the weight of the unsubstituted or substituted aniline. In the continuous downflow-mode procedure it can be useful not to completely hydrogenate the unsubstituted or substituted aniline, but to aim for a conversion of 80–97%.

The system comprising the reduced catalysts A and B which is used according to the invention displays very high operating lives; up to now lives of from 25000 to 30000 hours have been observed, and these experiments were terminated without noticeable lessening of the activity. These operating lives are a multiple of those described in the abovementioned EP-A 501 265 and EP-A 503 347.

Suitable starting materials for the process of the invention are unsubstituted or substituted anilines of the above formula (III). Examples of $C_1$–$C_4$-alkyl and $C_1$–$C_4$-alkoxy substituents which may be present are methyl, ethyl, propyl, isopropyl, butyl, isobutyl, methoxy, ethoxy, propoxy, isopropoxy, butoxy and isobutoxy. Of these, preference is given to methyl, ethyl, methoxy and ethoxy as substituents which may be present. The substituents are particularly preferably methyl or methoxy. Further preference is given to $R^2$=hydrogen while $R^1$ is as defined above. Very particular preference is given to hydrogenating unsubstituted aniline to give unsubstituted cyclohexylamine and unsubstituted dicyclohexylamine. The reaction mixtures obtained after the hydrogenation contain no cyclohexane, as long as this has not been added as solvent, so that particularly high contents of unsubstituted or substituted cyclohexylamine and unsubstituted or substituted dicyclohexylamine can be achieved. The hydrogenation mixtures can be worked up by simple distillation. For such a work-up, it can be advantageous not to react the unsubstituted or substituted aniline to completion. The incompletely reacted aniline can be returned to the reaction. The unconsumed proportion of the hydrogen used in 10–80-fold molar excess can also be returned to the reaction, with the major part of this unreacted hydrogen advantageously being recovered in a high-pressure separator so that the work of compression for the hydrogen does not need to be input again.

After separation by distillation, the unsubstituted or substituted cyclohexylamine and unsubstituted or substituted dicyclohexylamine prepared according to the invention are obtained in a purity of at least 99.9% by weight. In this purity, the specified compounds are generally usable for all further processes.

The degree to which the process of the invention can be varied is shown by a great increase in the proportion of unsubstituted or substituted dicyclohexylamine compared with the unsubstituted or substituted cyclohexylamine with increasing temperature under otherwise identical conditions. Thus, for example, the proportion of unsubstituted or substituted dicyclohexylamine in the temperature range of about 200°–240° C. is 1.5–5 times that in the temperature range of 140°–180° C. In the range of about 185°–210° C., the ratio of unsubstituted or substituted cyclohexylamine to unsubstituted or substituted dicyclohexylamine remains virtually constant in narrow limits even during a prolonged reaction time and is about cyclohexylamine:dicyclohexylamine= 1.5–6:1.

Example 1

An upright, heat-insulated high-pressure tube of stainless, acid-resistant steel having an internal diameter of 45 mm and a length of 1 m, which had beforehand been flushed oxygen-free using nitrogen, was charged with 1.4 l of a hydrogenation catalyst prepared by tabletting powders of cobalt, manganese, copper and barium oxides. The cobalt content of the pellets was 53% by weight, the manganese content was 14% by weight, the copper content was 0.2% by weight and the barium content was 0.9% by weight (remainder to 100% by weight: oxygen). The pellets had a cylinder height of 6 mm and a diameter of 6 mm, and a compressive strength of 553N/cm² on the cross-sectional surface and 156N, measured as force, on the cylindrical surface and also an internal surface area of 138 m²/g.

Downstream of this first high-pressure tube there was arranged, via a fixed high-pressure line, a second nitrogen-flushed, upright, heat-insulated high-pressure tube of stainless, acid-resistant steel having an internal diameter of 45 mm and a length of 1 m, which had been charged with 1.4 l of a hydrogenation catalyst prepared by tabletting powders of cobalt, manganese, silicon and magnesium oxides. The cobalt content of the pellets was 41% by weight, the manganese content was 4.1% by weight, the silicon content was 9.3% by weight and the magnesium content was 4.1% by weight (remainder to 100% by weight: oxygen). The pellets had a cylinder height of 3 mm and a diameter of 6 mm, and a compressive strength of 332N/cm² on the cross-sectional surface and 100N, measured as force, on the cylindrical surface and also an internal surface area of 168 m²/g.

To activate the two catalysts comprising different mixtures of metal oxides, the pellets were first dried together for 6 hours in a stream of nitrogen (temperature: max. 200° C., flow: 5 standard m³ of $N^2$/h). The actual activation was carried out under a nitrogen pressure of 200 bar at a temperature between 180° and 200° C. Hydrogen was gradually mixed into the inert gas, with its proportion not being allowed to exceed 10–15% by volume in the initial phase. Over a period of 24 hours, the proportion of nitrogen in the gas mixture was steadily reduced until finally pure hydrogen flowed through the reactor. The reaction was complete when water of reaction, which was collected in a separator downstream of the reactors, was no longer formed.

After activation of the hydrogenation catalysts, the hydrogen pressure in the two reactor systems, which were linked to one another in such a way that the aniline to be hydrogenated had to pass through both high-pressure tubes from the top downwards, was increased to 300 bar. Subsequently, 560 g/h of aniline together with 10 standard m³/h of hydrogen were pumped under a pressure of 300 bar through the high-pressure tubes connected in series, with the aniline being heated to a temperature of 160° C. in an upstream electrically heated heat exchanger prior to entering the first high-pressure tube. The reaction product leaving the second reaction tube was cooled in a second heat exchanger (water cooler) under 300 bar hydrogen pressure to a temperature <60° C. and in a gas separator was separated from excess hydrogen which could be returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (figures in % by area; the remainder to 100% is aniline and by-products):

| Operating time (h) | Temperature °C. | CHA*) (% by area) | DCHA*) (% by area) |
|---|---|---|---|
| 48 | 170 | 72.8 | 22.4 |
| 98 | 180 | 69.4 | 27.2 |
| 418 | 190 | 64.5 | 33.4 |
| 588 | 200 | 55.4 | 42.8 |
| 742 | 210 | 53.4 | 45.4 |
| 812 | 220 | 46.8 | 53.1 |

*)CHA = cyclohexylamine,
DCHA = dicyclohexylamine

Example 2

An upright, heat-insulated high-pressure tube of stainless, acid-resistant steel having an internal diameter of 90 mm and a length of 1.8 m, which had before-hand been flushed oxygen-free using nitrogen, was first charged with 10.26 l of a hydrogenation catalyst prepared by tabletting powders of cobalt, manganese, silicon and magnesium oxides. The cobalt content of the pellets was 35% by weight, the manganese content of the pellets was 4.9% by weight, the silicon content was 11% by weight and the magnesium content was 3.0% by weight (remainder to 100% by weight: oxygen). The pellets had a cylinder height of 3 mm and a diameter of 6 mm, and a compressive strength of 348N/cm$^2$ on the cross-sectional surface and a compressive strength of 100N, measured as force, on the cylindrical surface and also an internal surface area of 148 m$^2$/g.

Subsequently, 1.14 l of a hydrogenation catalyst prepared by tabletting powders of cobalt, manganese, copper and barium oxides were introduced on top of the first catalyst. The cobalt content of the pellets was 52% by weight, the manganese content was 16% by weight, the copper content was 0.18% by weight and the barium content was 0.91% by weight (remainder to 100%: oxygen). The pellets had a cylinder height of 7 mm and a diameter of 7 mm, and a compressive strength of 420N/cm$^2$ on the cross-sectional surface and of 160N on the cylindrical surface and also an internal surface area of 180 m$^2$/g.

After activation of the oxidic hydrogenation catalysts as in Example 1, the hydrogen pressure was increased to 300 bar. Subsequently, in the downflow mode, 2,280 g/h of aniline together with 70 standard m$^3$/h of hydrogen were pumped under a pressure of 300 bar through the high-pressure tube, with the aniline to be hydrogenated being heated to a temperature of 160° C. in an upstream electrically heated heat exchanger prior to entering the high-pressure tube. The reaction product leaving the reaction tube was cooled in a second heat exchanger (water cooler) to a temperature of <60° C. under 300 bar hydrogen pressure and was separated in a gas separator from excess hydrogen which was returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (the remainder to 100% is aniline and by-products):

| Operating time (h) | Temperature °C. | CHA*) (% by area) | DCHA*) (% by area) |
|---|---|---|---|
| 48 | 160 | 70.2 | 25.4 |
| 96 | 170 | 60.5 | 35.7 |
| 128 | 180 | 47.4 | 50.8 |
| 220 | 190 | 38.5 | 60.6 |
| 341 | 200 | 30.2 | 69.2 |
| 412 | 210 | 26.0 | 73.4 |
| 514 | 220 | 18.4 | 81.2 |

*)CHA = cyclohexylamine,
DCHA = dicyclohexylamine

Example 3

An upright, heat-insulated high-pressure tube of stainless, acid-resistant steel having an internal diameter of 90 mm and a length of 1.8 m, which had beforehand been flushed oxygen-free using nitrogen, was first charged with 1.14 l of a hydrogenation catalyst prepared by tabletting powders of cobalt, manganese, silicon and magnesium oxides. The cobalt content of the pellets was 35% by weight, the manganese content of the pellets was 4.9% by weight, the silicon content was 11% by weight and the magnesium content was 3.0% by weight (remainder to 100% by weight: oxygen). The pellets had a cylinder height of 3 mm and a diameter of 6 mm, and a compressive strength of 348N/cm$^2$ on the cross-sectional surface and a compressive strength of 100N, measured as force, on the cylindrical surface and also an internal surface area of 148 m$^2$/g.

Subsequently, 11.26 l of a hydrogenation catalyst prepared by tabletting powders of cobalt, manganese, copper and barium oxides were introduced on top of the first catalyst. The cobalt content of the pellets was 53% by weight, the manganese content was 14% by weight, the copper content was 0.2% by weight and the barium content was 0.9% by weight (remainder to 100%: oxygen). The pellets had a cylinder height of 7 mm and a diameter of 7 mm, and a compressive strength of 420N/cm$^2$ on the cross-sectional surface and of 160N on the cylindrical surface and also an internal surface area of 180 m$^2$/g.

After activation of the oxidic hydrogenation catalysts as in Example 1, the hydrogen pressure was increased to 300 bar. Subsequently, in the downflow mode, 2,280 g/h of aniline together with 70 standard m$^3$/h of hydrogen were pumped under a pressure of 300 bar through the high-pressure tube, with the aniline to be hydrogenated being heated to a temperature of 160° C. in an upstream electrically heated heat exchanger prior to entering the high-pressure tube. The reaction product leaving the reaction tube was cooled in a second heat exchanger (water cooler) to a temperature of <60° C. under 300 bar hydrogen pressure and was separated in a gas separator from excess hydrogen which was able to be returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (the remainder to 100% is aniline and by-products):

| Operating time (h) | Temperature °C. | CHA*) (% by area) | DCHA*) (% by area) |
|---|---|---|---|
| 48 | 180 | 82.2 | 9.89 |
| 96 | 190 | 85.4 | 12.70 |
| 114 | 200 | 90.6 | 9.3 |
| 136 | 210 | 84.9 | 14.6 |
| 224 | 220 | 81.2 | 18.2 |
| 364 | 230 | 74.2 | 24.4 |
| 568 | 240 | 70.2 | 28.2 |

*)CHA = cyclohexylamine,
DCHA = dicyclohexylamine

Example 4

An upright, heat-insulated high-pressure tube of stainless, acid-resistant steel having an internal diameter of 90 mm and a length of 1.8 m, which had before-hand been flushed oxygen-free using nitrogen, was first charged with 4.6 l of a hydrogenation catalyst prepared by tabletting powders of cobalt, manganese, silicon and magnesium oxides. The cobalt content of the pellets was 41% by weight, the manganese content was 5.4% by weight, the silicon content was 9.3% by weight and the magnesium content was 4.1% by weight (remainder to 100% by weight: oxygen). The pellets had a cylinder height of 6 mm and a diameter of 8 mm and a compressive strength of 305N/cm$^2$ on the cross-sectional surface and a compressive strength of 100N, measured as force, on the cylindrical surface and also an internal surface area of 165 m$^2$/g.

Subsequently, 6.8 l of a hydrogenation catalyst prepared by tabletting powders of cobalt, manganese, copper and barium oxides were introduced on top of the first catalyst. The cobalt content of the pellets was 53% by weight, the manganese content was 14% by weight, the copper content was 0.2% by weight and the barium content was 0.9% by weight. The pellets had a cylinder height of 7 mm and a diameter of 7 mm, and a compressive strength of 420N/cm$^2$ on the cross-sectional surface and of 160N on the cylindrical surface and also an internal surface area of 180 m²/g.

After activation of the oxidic hydrogenation catalysts as in Example 1, the hydrogen pressure was increased to 300 bar. Subsequently, in the downflow mode, 2,280 g/h of aniline together with 70 standard m³/h of hydrogen were pumped under a pressure of 300 bar through the high-pressure tube, with the aniline to be hydrogenated being heated to a temperature of 200° C. in an upstream electrically heated heat exchanger prior to entering the high-pressure tube. The reaction product leaving the reaction tube was cooled in a second heat exchanger (water cooler) to a temperature of <60° C. under 300 bar hydrogen pressure and was separated in a gas separator from excess hydrogen which was returned to the hydrogenation system. After further cooling to a temperature of <30° C. and depressurization to atmospheric pressure, the reaction product was analyzed by gas chromatography. Under steady-state reaction conditions, the following product composition was obtained (the remainder to 100% is aniline and by-products):

| Operating time (h) | Temperature °C. | CHA*) (% by area) | DCHA*) (% by area) |
|---|---|---|---|
| 163 | 199 | 73.64 | 25.57 |
| 3,828 | 197 | 73.01 | 26.06 |
| 6,114 | 185 | 73.80 | 22.86 |
| 9,062 | 210 | 76.93 | 21.00 |
| 16,462 | 185 | 71.16 | 22.62 |
| 19,805 | 195 | 73.50 | 22.70 |
| 25,167 | 210 | 72.51 | 23.10 |

*)CHA = cyclohexylamine,
DCHA = dicyclohexylamine

What is claimed is:

1. A process for preparing a mixture of a cyclohexylamine and a dicyclohexylamine of the formulae

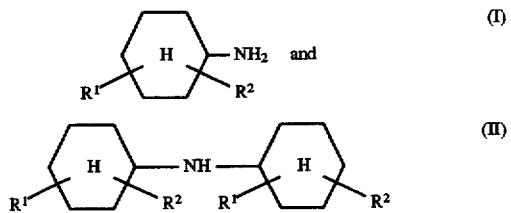

by catalytic hydrogenation of an aniline of the formula

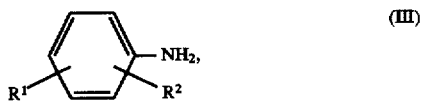

where, in the formulae, $R^1$ and $R^2$ are, independently of one another, hydrogen, $C_1$–$C_4$-alkyl or $C_1$–$C_4$-alkoxy, at a reaction temperature of from 140° to 260° C. and an $H_2$ pressure of from 10 to 400 bar, wherein the catalyst system used comprises two reduced, unsupported supported catalysts A+B comprising pressed element (hydr)oxide powders in which the following element proportions are present:

for catalyst A:
 40–60% by weight of one or more of Fe, Co, Ni;
 10–20% by weight of Mn;
 0.05–1.5% by weight of Cu; and
 0.2–5% by weight of one or more of Ca, Sr, Ba; and for catalyst B:
 30–50% by weight of one or more of Fe, Co, Ni;
 3–10% by weight of Mn;
 5–15% by weight of Si; and
 2–8% by weight of Mg;

where, in A and B, the remainder to 100% by weight is oxygen and the percentages are based on the total weight of the respective catalyst A or B.

2. The process of claim 1, wherein the element from the group consisting of Fe, Co and Ni which is used is Co or Ni or a Co/Ni mixture.

3. The process of claim 2, wherein the element from the group consisting of Fe, Co and Ni which is used is Co.

4. The process of claim 1, wherein the element from the group consisting of Ca, Sr and Ba which is used is Sr or Ba or an Sr/Ba mixture.

5. The process of claim 4, wherein the element from the group consisting of Ca, Sr and Ba which is used is Ba.

6. The process of claim 1, wherein the catalysts A and B have a compressive strength of 200–800N/cm² on flat pressed surfaces, a compressive strength of 50–200N, measured as force, on curved pressed surfaces and an internal surface area of 30–200 m².

7. The process of claim 6, wherein the compressive strength on flat pressed surfaces is 250–600N/cm².

8. The process of claim 6, wherein the compressive strength on curved pressed surfaces, measured as force, is 80–140N.

9. The process of claim 6, wherein the internal surface area is 80–160 m²/g.

10. The process of claim 1, wherein the catalyst A and B are used in a weight ratio of from 0.5 A:9.5 B to 9.5 A:0.5 B.

11. The process of claim 1, wherein the reaction is carried out continuously in the downflow mode over fixed-bed catalysts and the weight hourly velocity is 0.1–3 kg of aniline per liter of catalyst and hour.

12. The process of claim 11, wherein the weight hourly velocity is 0.15–1.5 kg of aniline per liter of catalyst and hour.

13. The process of claim 1, wherein the reaction is carried out at an $H_2$ pressure of 20–350 bar.

14. The process of claim 13, wherein the $H_2$ pressure is 100–300 bar.

15. The process of claim 1, wherein the reaction is carried out at a temperature of 160°–230° C.

16. The process of claim 1, wherein the catalyst A and B are, prior to use, reduced separately or together by treatment with hydrogen at 160°–240° C. and 10–400 bar, with the hydrogen being used as $H_2$/inert gas mixture at the beginning of the reduction and the proportion of inert gas being completely removed during the course of the reduction.

17. The process of claim 1, wherein the unsubstituted or substituted aniline is diluted with 10–100% by weight of a reaction-inert solvent, based on the unsubstituted or substituted aniline.

18. The process of claim 17, wherein the unsubstituted or substituted aniline is diluted with 10–40% by weight of a reaction-inert solvent, based on the unsubstituted or substituted aniline.

* * * * *